United States Patent [19]

Peters et al.

[11] Patent Number: 4,652,595
[45] Date of Patent: Mar. 24, 1987

[54] PROCESS AND APPARATUS FOR THE PREPARATION OF MIXTURES OF ISOCYANATE AND WATER WHICH ARE STABLE FOR A SHORT TIME FOR GLUEING PARTICULATE MATERIAL, IN PARTICULAR CHIPS, FIBERS OR THE LIKE

[75] Inventors: Robert Peters, Cologne; Klaus Schulte, Leverkusen; Hanns I. Sachs; Peter Kasperek, both of Cologne, all of Fed. Rep. of Germany

[73] Assignee: Bayer Aktiengesellschaft, Leverkusen, Fed. Rep. of Germany

[21] Appl. No.: 736,162

[22] Filed: May 20, 1985

[30] Foreign Application Priority Data

Jun. 6, 1984 [DE] Fed. Rep. of Germany ....... 3420997

[51] Int. Cl.$^4$ ............................................ C08G 18/08
[52] U.S. Cl. .................................... 523/315; 523/319; 524/839; 239/310
[58] Field of Search ....................... 523/315, 313, 319; 524/839

[56] References Cited

U.S. PATENT DOCUMENTS 3,294,724 12/1966 Axelrood ............................ 524/839
4,303,569 12/1981 Güurak ............................... 523/315

FOREIGN PATENT DOCUMENTS 2344135 3/1975 Fed. Rep. of Germany ...... 524/839

Primary Examiner—C. Warren Ivy
Attorney, Agent, or Firm—Gene Harsh; Joseph C. Gil; Aron Preis

[57] ABSTRACT

The present invention relates to a process for the preparation of mixtures of isocyanate and water which are stable for a short time for glueing particulate material, in particular chips, fibers, or the like, in which isocyanate is injected at high pressure into the water, characterized in that the water is delivered to the site of injection as a stream under low pressure, and to an apparatus for carrying out such process.

2 Claims, 1 Drawing Figure

PROCESS AND APPARATUS FOR THE PREPARATION OF MIXTURES OF ISOCYANATE AND WATER WHICH ARE STABLE FOR A SHORT TIME FOR GLUEING PARTICULATE MATERIAL, IN PARTICULAR CHIPS, FIBERS OR THE LIKE

BACKGROUND OF THE INVENTION

This invention relates to a process and an apparatus for the preparation of mixtures of isocyanate and water which are stable for a short time for glueing particulate material, in particular chips, fibers or the like, in which isocyanate is injected into the water at a high pressure.

The preparation of such mixtures for the above-mentioned purpose is difficult because isocyanate is immiscible with water except under certain conditions. The process of mixing must at present be carried out with high technical expenditure by the high pressure technique, using the counterflow injection method. Expensive high pressure pumps are required for dosing the two components. Mixing takes place in a counterflow injection mixing head at pressures from about 100 to 300 bar and the mixture is subsequently applied to the chips either by means of airless spray nozzles or pressure-free, with or without the assistance of air. Part of the energy expended is thus utilized for atomizing the mixture but the expenditure in apparatus is nevertheless very high. Due to the high level of energy employed, the apparatus is subject to severe stress and wear, and considerable servicing and maintenance is required in particular for the parts of the apparatus which carry water.

It is an object of the present invention to develop a simple process and inexpensive, trouble-free apparatus for preparing a mixture of isocyanate and water which is stable for a short time.

BRIEF DESCRIPTION OF THE DRAWING

The drawing represents one embodiment of the present invention.

DESCRIPTION OF THE INVENTION

Figure 1:
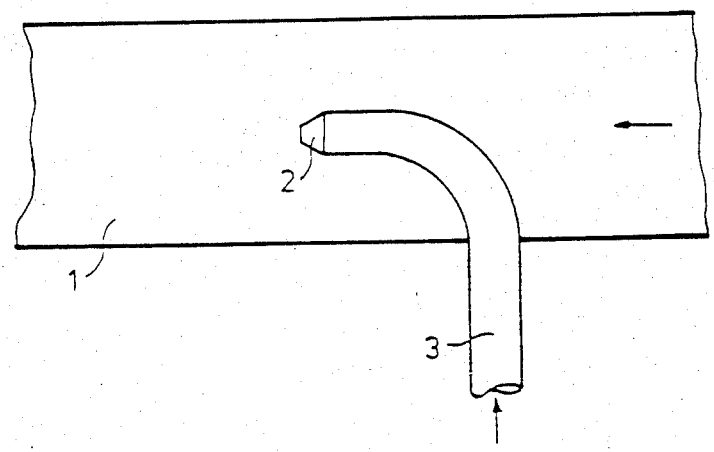

It has surprisingly been found that the above-noted problem is solved by delivering water as a low pressure stream to the site of injection.

This means that the water need not be atomized in order to be mixed with the isocyanate. Only the isocyanate is atomized at high pressure as it is injected into the stream of water which is at a low pressure. It was completely unexpected to find that a mixture which is sufficiently stable for a short time for glueing the chips, with or without the assistance of air, could be obtained by such simple means.

According to one particular embodiment of the new process, the atomization pressure of the isocyanate is maintained above 50 bar and the pressure of water below 10 bar, preferably below 3 bar. These pressure conditions have proved to be advantageous for the preparation of a homogeneous mixture which is stable for a short time.

According to another, particular embodiment of the process, the isocyanate is injected at least approximately in the direction of flow of the water. This procedure avoids any additional increase of pressure in the stream of water.

The new apparatus for the preparation of mixtures of isocyanate and water for glueing particulate material, in particular chips, fibers or the like, comprises feed pipes for water and isocyanate and a nozzle arranged at the end of the isocyanate feedpipe. The innovation resides in the fact that the nozzle is directed into the water feedpipe.

This embodiment of the apparatus is substantially simpler and more trouble-free. Simple pumps, e.g. gear wheel pumps or adjustable control valves may be used for dosing the water. A high pressure pump of course continues to be necessary for delivering the isocyanate.

According to one particular embodiment, the nozzle is directed into the water feedpipe at least approximately in the direction of flow of the water. The parts of the apparatus are thereby subjected to less stress.

An exemplary embodiment of the new apparatus is illustrated purely schematically in the drawing. The nozzle 2 of an isocyanate feedpipe 3 opens into a feedpipe 1 carrying water. Feedpipe 1 is connected to a gear wheel pump (not shown) while the isocyanate feedpipe 3 is connected to a high pressure pump. Feedpipe 1 carries the mixture of isocyanate and water into a bonding mixer (not shown) containing wood chips. The water is delivered at a pressure of 2 bar and the isocyanate is atomized at 150 bar.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of mixtures of isocyanate and water suitable for glueing particulate material, in particular chips, fibers or the like, in which water-miscible isocyanate is injected at a pressure of above 50 bar into the water, characterized in that the water is delivered to the site of injection as a stream under a pressure below 10 bars.

2. The process of claim 1, characterized in that the isocyanate is injected at least approximately in the direction of flow of the water.

* * * * *